(12) United States Patent
Ylänen et al.

(10) Patent No.: US 6,517,857 B2
(45) Date of Patent: Feb. 11, 2003

(54) BIOACTIVE PRODUCT AND ITS USE

(76) Inventors: Heimo Ylänen, Skepparegatan 2 A 30, FIN-20810 Åbo (FI); Hannu Aro, Valtaojantie 4, FIN-20810 Turku (FI); Kaj Karlsson, Dragonvägen 48, FIN-20720 Turku (FI); Antti Yli-Urpo, Värttinäkatu 17, FIN-20660 Littoinen (FI); Mikko Hupa, Rakuunatie 47, FIN-20720 Turku (FI); Egon Nordström, Norrskogsvägen 3, FIN-21600 Pargas (FI)

( * ) Notice: Subject to any disclaimer, the term of this patent is extended or adjusted under 35 U.S.C. 154(b) by 0 days.

(21) Appl. No.: 09/875,017

(22) Filed: Jun. 7, 2001

(65) Prior Publication Data

US 2001/0041325 A1 Nov. 15, 2001

Related U.S. Application Data

(63) Continuation of application No. PCT/FI99/00961, filed on Nov. 19, 1999.

(30) Foreign Application Priority Data

Dec. 11, 1998 (FI) .................................................. 982684

(51) Int. Cl.⁷ .............................. A61F 2/00; A61F 2/02; A61F 2/28

(52) U.S. Cl. ........................ 424/422; 424/423; 424/424; 424/425; 424/426

(58) Field of Search ................................. 424/422, 423, 424/426, 424, 425; 604/891.1; 507/1; 65/17.3

(56) References Cited

U.S. PATENT DOCUMENTS

| 4,604,097 A | 8/1986 | Graves, Jr. et al. ........... 623/11 |
| 5,108,957 A | 4/1992 | Cohen et al. .................. 501/35 |
| 6,248,344 B1 | 6/2001 | Ylanen et al. ............... 424/423 |

FOREIGN PATENT DOCUMENTS

| EP | 591/696 | 4/1994 |
| FI | 971692 | 4/1997 |
| WO | WO 91/12032 | 8/1991 |
| WO | WO 95/14127 | 5/1995 |
| WO | WO 96/21628 | * 7/1996 |

* cited by examiner

Primary Examiner—Thurman K. Page
Assistant Examiner—Rachel M. Bennett
(74) Attorney, Agent, or Firm—James C. Lydon

(57) ABSTRACT

A porous textile product made from bioactive glass fibers. The fibers in the product are of at least two types, fiber A and fiber B, with fiber A being made from a bioactive glass, and fiber B being made from a weakly bioactive glass.

15 Claims, No Drawings

BIOACTIVE PRODUCT AND ITS USE

This application is a continuation of International application PCT/FI99/00961, filed Nov. 19, 1999 and published on Jun. 22, 2000 in the English Language.

The invention relates to the porous textile product made from bioactive glass fiber, defined in claim 1. The invention further relates to the use of the said textile product.

BACKGROUND OF THE INVENTION AND THE STATE OF THE ART

The publications to which reference is made below and which are used for illustrating the background of the invention and the state of the art are to be deemed as being incorporated into the description of the invention below.

Biomaterials and their Biologic Attachment

Implants for both medical and dental purposes have long been prepared from a variety of materials. Various metals, metal alloys, plastics, ceramic materials, glass ceramic materials, and the latest, i.e. bioactive glasses, differ one from another not only by their durability but also by the properties of the interface between the implant and the tissue. Inert materials, such as metals and plastics, do not react with a tissue, in which case there always remains an interface between the implant and the tissue; the implant and the tissue constitute two distinct systems. Bioactive materials, such as hydroxyapatite, glass ceramic materials and bioactive glasses, react chemically with the tissue, whereupon there forms at the interface between the implant and the tissue a chemical bond, which is relatively strong, especially with bioactive glasses. The implant and the tissue are thus fixed to each other. The speed of the healing of the tissue and the possible chemical bond with the implant depend on the tissue activity of the implant material used.

International patent publication WO 96/21628, Brink et al., describes a group of bioactive glasses which can be processed easily. From such bioactive glasses it is possible, for example to draw fibers and, for example by the torch spraying technique, to prepare so-called microspheres of glass. Porous bioactive pieces are prepared by sintering these microspheres together. By using microspheres which are within as narrow a fraction as possible (of as uniform a size as possible), it is possible to control the porosity of the body. According to the literature it seems that the most advantageous particle size is within the fraction 200–400 microns (Schepers et al. 1997, Tsuruga et al. 1997, Schliephake et al. 1991, Higashi et al. 1996). The studies carried out by the inventors so far have shown that a porous bioactive implant which has been prepared by sintering bioactive microspheres of the fraction 250–300 microns reacts very strongly in the femur of a rabbit (Ylänen et al. 1997). The results of the studies have shown that the said implant model reacts rapidly and the porous matrix fills at a steady speed with new bone. The shear strength of the bioactive implants in a push-out to failure test has been already after three weeks statistically as high as after 12 weeks. The amount of bone inside the matrix has been after 12 weeks 35–40% of the pore volume both in bioactive implants and in the titanium implants used as controls. It is, however, advisable to note that in a bioactive matrix porosity increases evenly as a function of time as the bioactive glass mass decreases. Porosity increased in experiments in vivo from 30% to 65%. The porosity of titanium, of course., does not change in any way. Thus the amount of new bone inside bioactive implants is de facto almost double that inside titanium implants. In our opinion this shows that the porous implant type used by us is right.

The beginning of new bone growth seems to be located in micro-cracks in the bioactive glass particles (Schepers et al. 19967). Evidently the calcium and phosphate dissolving from the glass into the fluid (in vitro SBF, in vivo plasma) surrounding the micro-crack quickly form, together with the calcium and phosphate normally in the fluid, so high a concentration that the solubility product of the ions concerned is exceeded. As a consequence of this, calcium phosphate precipitates onto the silica gel on the surface of the bioactive glass and new bone growth begins. The porous body sintered from bioactive microspheres is full of microscopically small cavities. This explains the rapid bone growth inducing property of the tested bodies we sintered from bioactive microspheres. It has further been shown that the roughness of the surface has a favorable effect on the attachment to the biomaterial surface of proteins which control bone growth (Grossner et al. 1991, Boyan et al. 1998), as well as has the biomaterial itself. According to the literature, the said proteins attach best and most rapidly to the surface of bioactive glass (Ohgushi et al. 1993, Vrouwenvelder et al. 1992, Lobel et al. 1998, Vrouwenvelder et al. 1993, Shimizu et al. 1997, Miller et al. 1991).

Patent publication WO 98/47465 describes a porous composite which comprises i) particles A made from a bioactive material and ii) particles B which are made from a non-bioactive or weakly bioactive material sintrable to the said bioactive material. The said particles A and particles B are sintered together to form a porous composite. Combined with the implant, the said composite ensures both rapid ossification and permanent attachment of the implant. The composite described here, being made up of smooth glass spheres with untreated surfaces, must, however be in contact with body fluid for about a week before the silica gel layer required by bone growth is formed on the sphere surfaces. Only thereafter can the actual bone formation begin.

OBJECT OF THE INVENTION

It is an object of the invention to provide a novel bioactive and porous textile product which ensures more rapid ossification than do prior art composites.

It is a particular object of the invention to provide a bioactive porous textile product having already, on the surface of its fibers, a bioactive layer required for the initiation of bone growth, in which case the integration of the bone to the composite can begin immediately after the composite comes into contact with body fluid, i.e. immediately after the surgery.

It is a further object of the invention to provide a bioactive porous product which is easy to mold and which, after the molding, can when necessary be hardened to the desired shape.

SUMMARY OF THE INVENTION

The characteristics of the invention are given in the independent claims.

The invention thus relates to a porous textile product made from bioactive glass fibers. It is characteristic that the fibers therein are of at least two kinds, fiber A and fiber B, fiber A being made of a bioactive glass and fiber B being made of a weakly bioactive glass.

The invention further relates to the use of the novel textile product as an implant, a product yielding a drug or some other substance at a controlled rate, for tissue control, as filler material in bone cavities or in soft tissue, for the removal of pulpa, as dental root filler material, or as binding material for bone transplants.

PREFERRED EMBODIMENTS OF THE INVENTION AND A DETAILED DESCRIPTION

Definitions

By the term "implant" is meant in the present invention any body, made of an man-made material, to be placed in a tissue, such as an artificial joint or part thereof, a screw, a fixation plate, or a corresponding orthopedic or dental device.

In the context of the definition of the present invention, by "bioactive glass" is meant a glass which in physiological conditions dissolves at least partly in a few months, preferably within a few weeks, most preferably in approximately 6 weeks.

In the context of the definition of the present invention, the term "weakly bioactive glass" denotes a glass which in physiological conditions does not dissolve within the first months, at least not completely.

Especially Preferred Embodiments

The surface of the fibers forming the textile product, especially the surface of the fibers made of bioactive glass, should preferably be roughened, for example, by using hydrogen fluoride vapor. The roughening can be carried out before the making of the textile or thereafter. The topographic irregularities produced in the surface by the roughening are typically within the range 1–50 microns.

According to another embodiment, there is formed on the fiber surfaces one or more bioactive layers, which are made up of, for example, silica gel and/or hydroxyapatite. Even though it is possible to form such bioactive layers on the surfaces of smooth fibers, it is, however, preferable that the fiber surface is first roughened. Such pre-corrosion, i.e. the forming of a bioactive layer, may be achieved, for example, by means of simulated body fluid (SBF) or some organic or inorganic solvent.

According to one preferred embodiment, there is added to the bioactive layer some bone growth inducing substance, typically a protein, such as some growth factor or the like.

Alternatively, it is possible to add to the bioactive layer a drug or some other substance. In this case the textile product may serve as a product which yields the said substance at a controlled rate.

It is possible to add foreign substances to the bioactive layer before a textile product is made from the fiber, but preferably such substances are added to the textile product itself.

Many conventional bioactive glasses involve the problem that their processability is poor, since they crystallize easily. It is not possible to draw fibers from such bioactive glasses. The fibers may be manufactured by technology known per se.

International patent application publication WO 96/21628 describes bioactive glasses of a novel type; their working range is suitable for the processing of glass, and they can thus be used for making fibers. The bioactive glasses described in the said publication are especially good also for the reason that the processability of the glass has been achieved without the adding of aluminum oxide. Such glasses typically have the following composition:

$SiO_2$ 53–60% by weight
$Na_2O$ 0–34% by weight
$K_2O$ 1–20% by weight
$MgO$ 0–5% by weight
$CaO$ 5–25% by weight
$B_2O_3$ 0–4% by weight
$P_2O_5$ 0.5–6% by weight however so that $Na_2O+K_2O$=16–35% by weight,
$K_2O+MgO$=5–20% by weight and
$MgO+CaO$=10–25% by weight.

According to an especially preferred embodiment, the bioactive glass fibers are made from a bioactive glass the composition of which is $Na_2O$ 6% by weight, $K_2O$ 12% by weight, $MgO$ 5% by weight, $CaO$ 20% by weight, $P_2O_5$ 4% by weight and $SiO_2$ 53% by weight.

The material of fiber type B, i.e. the weakly bioactive glass, is preferably such that it will begin to dissolve before the bioactive glass (the material of fiber type A) has dissolved completely.

Fiber type B of the textile product is preferably made of a weakly bioactive glass having the composition $Na_2O$ 6% by weight, $K_2O$ 12% by weight, $MgO$ 5% by weight, $CaO$ 15% by weight, $P_2O_5$ 4% by weight and $SiO_2$ 58% by weight.

The textile product according to the invention may, of course, contain fibers made from a plurality of bioactive glasses and/or fibers made from a plurality of weakly bioactive glasses. It may additionally contain other types of fibers, such as fibers made of a biodegradable thermoplastic polymer.

The textile product is preferably such that the length of the fibers therein varies. Preferably the order of the fibers in the product is not predetermined.

According to an especially preferred embodiment, the textile product is a felt, fabric or mat manufactured by, for example, the non-woven technique. The manufacture of the fabric is carried out by drawing shorter or longer fibers from glass. Non-woven fabric is made by spraying shorter fibers to form a mat.

The textile product according to the invention may suitably be impregnated with a substance, for example simulated body fluid or a collagen adhesive, which causes the product to harden after the product has been molded into the desired shape. As a consequence of such impregnation there is obtained an apatite junction at the intersections of the fibers.

The textile product according to the invention can be used in many fields. Some of the most important applications are its use as an implant, as a product which yields a drug or another substance at a controlled rate, for the control of tissues, as a filler material in bone cavities or soft tissue, in the removal of pulpa, as a dental root filler material, or as a binding agent for bone transplant. Overall, it can be noted that the textile product according to the invention is intended for being brought into contact with an individual's tissue or body fluid.

The textile product according to the invention is, not only in the micro size (fibers) but also in the macro size (textile product made from fibers), full of independent islands favorable to new bone growth. A pre-roughened and pre-activated surface further promotes the initiation of reactions indispensable for new bone growth.

The invention embodiments mentioned above are only examples of the implementation of the idea according to the invention. For a person skilled in the art it is clear that the various embodiments of the invention may vary within the framework of the claims presented below.

Literature References

Schepers E J and Ducheyne P (19967) Bioactive glass particles of narrow size range for the treatment of oral bone defects: a 1–24 month experiment with several materials and particle sizes and size ranges. *J Oral Rehabil*, 24(3):171–181.

Tsuruga E, Takita H, Itoh H, Wakisaka Y and Kuboki Y (1967) Pore size of porous hydroxyapatite as the cell-substratum controls BMP-induced osteogenesis. *J Biochem* (Tokyo) 121(2):317–324.

Schliephake H, Neukam F W and Klosa D (1991) Influence of pore dimensions on bone ingrowth into porous hydroxylapatite blocks used as bone graft substitutes. A histometric study. *Int J Oral Maxillofac Surg* 20(1): 53–58.

Higashi T and Okamoto H (1996) Influence of particle size of hydroxyapatite as a capping agent on cell proliferation of cultured fibroblasts. J Endod 22(5):236–239.

Yllänen H, Karlsson K H, Heikkilä J T, Mattila K and Aro H T (1997) 10th International Symposium on Ceramics in Medicine, Paris.

Grossner-Schreiber B and Tuan R S (1991) The influence of the titanium implant surface on the process of osseointegration. *Dtsch Zahnartzl Z* 46(10):691–693.

Boyan B D, Batzer R, Kieswetter K, Liu Y, Cochran D L, Szmuckler-Moncler S, Dean D D and Schwartz Z (1998) Titanium surface roughness alters responsiveness of MG63 osteoblast-like cells to alpha, 25-(OH)2D3. *J Biomed Mater Res* 39(1):77–85.

Ohgushi H, Dohi Y, Tamai S and Tabata S (1993) Osteogenic differentiation of marrow stromal stem cells in porous hydroxyapatite ceramics. *J Biomed Mater Res* 27(11): 1401–1407.

Vrouwenvelder W C, Groot C G and de Groot K (1992) Behaviour of fetal rat osteoblasts cultured in vitro on bioactive glass and nonreactive glasses. *Biomaterials* 13(6):382–392.

Lobel K D and Hench L L (1998) In vitro adsorbition and activity of enzymes on reaction layers of bioactive glass substrates. *J Biomed Mater Res* 39(4):575–579.

Vrouwenvelder W C, Groot C G and de Groot K (1993) Histological and biochemical evaluation of osteoblasts cultured on bioactive glass, hydroxylapatite, titanium alloy and stainless steel. *J Biomed Mater Res* 27(4): 465–475.

Shimizu Y, Sugawara H, Furusawa T, Mizunuma K Inada K and Yamashita S (1997) Bone remodeling with resorbable bioactive glass and hydroxyapatite. *Implant Dent* 6(4): 269–274.

Miller T A, Ishida K, Kobayashi M, Wollman J S, Turk A E and Holmes R E (1991) The induction of bone by an osteogenic protein and the conduction of bone by porous hydroxyapatite: a laboratory study in the rabbit. *Plast Reconstr Surg* 87(1):87–95.

What is claimed is:

1. A porous textile product made from bioactive glass fibers, wherein the fibers therein are of at least two types, fiber A and fiber B, in which fiber A comprises a bioactive glass, and fiber B comprises a weakly bioactive glass which in physiological conditions does not completely dissolve within the first few months.

2. The textile product of claim 1, wherein the surface of at least one fiber is roughened.

3. The textile product of claim 1, wherein there are one or several bioactive layers formed on the surface of at least one type of fiber.

4. The textile product of claim 3, wherein the layer is made up of silica gel and/or hydroxyapatite.

5. The textile product of claim 3, wherein a bone growth inducing substance has been added to said bioactive layer.

6. The textile product of claim 3, further comprising a drug added to the textile product.

7. The textile product of claim 1, wherein fiber A is made of a bioactive glass having a composition comprising $Na_2O$ 6% by weight, $K_2O$ 12% by weight, MgO 5% by weight, CaO 20% by weight, $P_2O_5$ 4% by weight, and $SiO_2$ 53% by weight.

8. The textile product of claim 1 wherein fiber B is made of a weakly bioactive glass having a composition comprising $Na_2O$ 6% by weight, $K_2O$ 12% by weight, MgO 5% by weight, CaO 15% by weight, $P_2O_5$ 4% by weight, and $SiO_2$ 58% by weight.

9. The textile product of claim 1, wherein a length of the fibers therein varies and an order of the fibers in the product is not predetermined.

10. The textile product of claim 1, wherein the textile product is a felt, fabric or mat.

11. The textile product of claim 10, wherein said product is made by a non-woven technique.

12. The textile product of claim 1, wherein said product is impregnated with a substance which causes the product to harden after the product has been molded into a desired shape.

13. A method for forming a chemical bond between an implant and the body tissue of an individual, comprising forming the textile product of claim 1, into a shaped textile product suitable for implantation into an individual, and implanting said shaped textile product into an individual such that said shaped textile product comes into contact with body fluid of said individual.

14. The method of claim 13, wherein said textile product is selected from the group consisting of a product which releases a substance at a controlled rate, a product for the control of tissues, a product suitable for use as a filler in bone cavities or soft tissue, a product suitable for use as a dental root filler material, and a product suitable for use as a binding agent for bone transplants.

15. The textile product of claim 2, wherein the fiber whose surface is roughened is fiber A.

* * * * *